United States Patent [19]

Carrasco

[11] Patent Number: 4,897,358

[45] Date of Patent: Jan. 30, 1990

[54] TISSUE STORAGE SYSTEM

[76] Inventor: Jose I. Carrasco, P.O. Box 4804, San Juan, P.R. 00905

[21] Appl. No.: 803,431

[22] Filed: Dec. 2, 1985

[51] Int. Cl.[4] .............................................. C12M 1/24
[52] U.S. Cl. ...................................... 435/296; 220/23; 220/23.4
[58] Field of Search ................ 220/23, 23.4, 408, 410, 220/DIG. 14; 435/296, 284, 292; 215/227

[56] References Cited

U.S. PATENT DOCUMENTS

| | | | |
|---|---|---|---|
| 876,427 | 1/1908 | Benson | 220/23 |
| 1,541,799 | 6/1925 | Dodge | 220/408 |
| 1,957,153 | 5/1934 | Smiley, Jr. | 220/97 |
| 2,574,692 | 11/1951 | Davidson et al. | 312/345 |
| 3,367,484 | 2/1968 | Nelson | 220/23 |
| 3,593,861 | 7/1971 | Holland, Jr. | 214/10.5 R |
| 3,955,681 | 5/1976 | DeZinno | 211/13 |
| 4,195,732 | 4/1980 | Bell | 206/391 |
| 4,296,205 | 10/1981 | Verma | 435/296 |
| 4,299,920 | 11/1981 | Peters | 435/284 |
| 4,308,351 | 12/1981 | Leighton et al. | 435/284 |
| 4,321,330 | 3/1982 | Baker et al. | 435/284 |
| 4,339,537 | 7/1982 | Sogi et al. | 435/240 |
| 4,348,421 | 9/1982 | Sakakibarce et al. | 220/23 |
| 4,391,912 | 7/1983 | Yoshida et al. | 435/284 |
| 4,636,328 | 1/1987 | Flynn et al. | 215/227 |

FOREIGN PATENT DOCUMENTS

2434089  1/1976  Fed. Rep. of Germany ..... 220/23.4

Primary Examiner—Noah P. Kamen
Attorney, Agent, or Firm—Rodman & Rodman

[57] ABSTRACT

The tissue sample storage system includes a tissue sample container that is detachably secured in a tray member. The tissue sample container has a cover member with at least one recess for receiving an auxiliary container and a base portion with provision for detachable engagement with a rail in the tray member. The container base portion can include either a recess or a projecting portion and the tray member rail is of complementary engaging configuration. The tissue sample storage system also includes stacking members for stacking one tray member upon another tray member.

21 Claims, 6 Drawing Sheets

TISSUE STORAGE SYSTEM

This invention relates to devices for holding biological specimens and more particularly to a tissue sample storage system including a container for storing tissue samples and a holding tray in which the tissue sample containers are detachably secured.

In numerous areas of medical treatment it is often necessary to remove a portion of body tissue for further examination or testing. The removed tissue may not receive immediate attention and therefore must be preserved and stored for later use. This is usually accomplished by placing the tissue sample in a container of chemical preservative, the size of the container corresponding to the size of the tissue sample.

Oftentimes tissue samples may be obtained by one physician and examined and tested by another physician such as a pathologist. Generally a hospital will obtain several tissue samples during one part of the day when operations are scheduled, and thereafter deliver such samples to a pathology department.

As the tissue samples accumulate, the containers which house the tissue samples can be placed in a holding tray or delivery basket. Each tissue sample container must be individually identified by appropriate information necessary for the pathologist's examination, including an indication of the source of the tissue, and positive identification of the patient from whom the sample was removed.

If the tissue sample container is sufficiently large a label can be adhered, taped or otherwise secured directly to the tissue sample container. With smaller tissue sample containers, the label may be larger than the container, and if several small containers are assembled together, the labels may interfere and come loose resulting in one or more tissue sample containers with detached labels. Once a label for a tissue sample container is detached it can easily be lost or misassociated with another tissue sample container.

If a large number of tissue sample containers are accumulated, more than one holding tray may be used. Trays for holding tissue sample containers are often stacked one on top of another. Generally several tissue sample containers in a holding tray vary in size, and when one holding tray is stacked onto another, an unstable stacking arrangement results. During delivery of the holding trays from one location to another the tissue sample containers can tip over, with possible leakage of the chemical preservative, and contamination or spoilation of the tissue samples, as well as contamination of personnel that handle the trays.

Occasionally it is necessary for a pathologist to perform several separate and distinct tests on a tissue sample. Plural testing may require that the tissue sample be divided into two or more parts. The source of the divided samples must be known and each smaller sample should be correlated with the original sample. However it may also be necessary to keep the divided samples separated from the original sample. Therefore additional tissue sample storage containers must be provided for each divided sample along with separate additional identification labels. The need for additional containers and labels when an extensive analysis is performed presents further possibilities for mixup and confusion in the identification and correlation of such tissue samples.

It is thus desirable to provide a system for storing tissue samples that conveniently and separately accommodates several tissue samples cut from a main sample in containers that can be firmly secured in a holding tray that can be stacked in a stable fashion upon other holding trays. Such an arrangement would also minimize actual handling of the specimen by different persons since the specimens would be readily available and transported in place.

OBJECTS AND SUMMARY OF THE INVENTION

Among the several objects of the invention may be noted the provision of a novel tissue sample storage system, a novel tissue sample storage system including a tissue sample container and holding tray having gripping means for firmly securing the tissue sample container to the holding tray, novel tissue sample storage system including a container that accommodates a plurality of auxiliary tissue sample storage containers, a novel tissue sample storage system having stackable holding trays, a novel tissue sample storage system which prevents tissue sample storage containers from tipping over in a holding tray, and a novel tissue sample storage system wherein all of the tissue sample containers are readily available for inspection, identification and tallying purposes.

Other objects and features of the invention will be in part apparent and in part pointed out hereinafter.

The present invention relates to a system for storing tissue samples.

In one embodiment of the invention, a tissue sample container includes a cover member preferably hinged to a wall portion of the container. The cover member is provided with at least one cover member recess for accommodating an auxiliary container. However, the auxiliary container does not communicate with the inside of the container structure. Under this arrangement a main tissue sample can be kept in the container and separate other samples can be kept in the auxiliary containers held by the container cover. Thus a particular sample which has been divided into smaller samples can be kept together to minimize the risk of misplacement or lost identification.

A base portion of the container includes a recess arranged to detachably grip upon a rail provided in a holding tray thereby firmly securing the container in the tray. In another embodiment of the invention the rail structure in the tray includes a recess and a projection is formed at the base of the container to detachably engage the rail recess. In either embodiment the tissue sample container is snapped in place into the holding tray in a predetermined position.

The rail or rails of the holding tray are preferably elongated to permit slidable movement of the containers in the tray if repositioning is desired. However, during any such repositioning the container is detented in the tray by engagement with the rail of the tray and thus cannot tip over.

The tray member is a shallow basket-like structure with a plurality of sections, each section accommodating a row of the tissue sample storage containers. The elongated rail for engaging the base of the container member is provided at the bottom of the tray member. The rail can also be used to support the tissue sample container in the tray member as well as secure the tissue sample storage container in the tray member.

Preferably each section of the tray member is of equal width. However the tissue sample container members may be of varying height and length, but of uniform width.

The tray member also includes removable support members provided at each corner for supporting a second tray member in spaced relationship from the first tray member. A plurality of tray members can thus be stacked one upon another in stable fashion such that the contents of one tray member do not interfere with the bottom portion of another tray member stacked thereon.

The tissue sample container member is preferably formed of a transparent plastic material that is not deleteriously affected by chemical preservatives or sterilization treatments.

The invention accordingly comprises the constructions hereinafter defined, the scope of the invention being indicated in the concluding claims.

DESCRIPTION OF THE DRAWINGS

In the accompanying drawings, in which various possible embodiments of the invention are illustrated.

Corresponding reference characters indicate corresponding parts throughout the several views of the drawings.

DETAILED DESCRIPTION OF THE INVENTION

Figure 1:
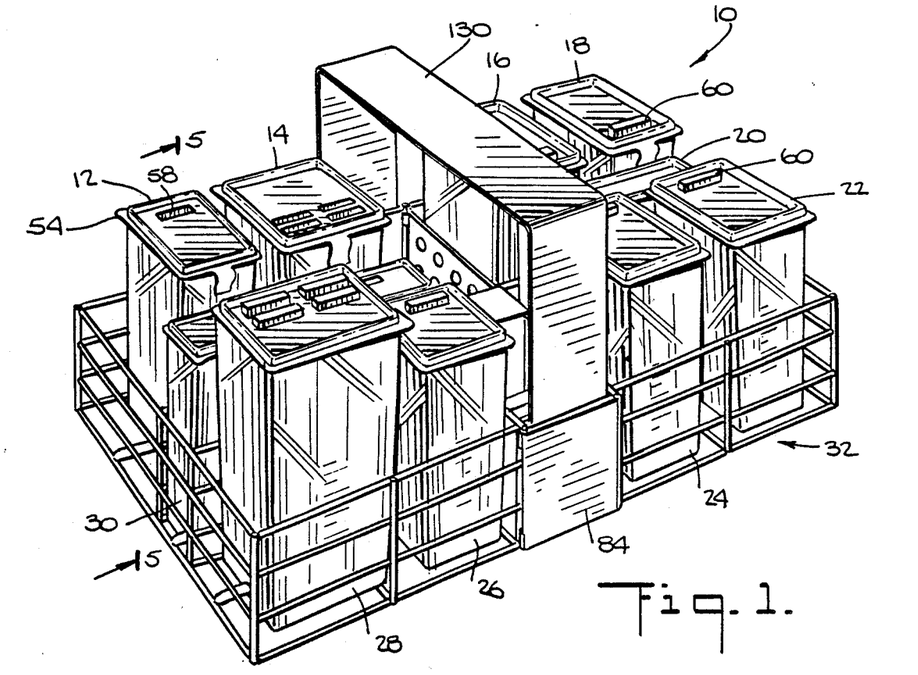
FIG. 1 is a perspective view of a tissue sample storage system.

Referring to the drawings, a tissue sample storage system is generally indicated by the reference number 10 in FIG. 1.

The system 10 includes plurality of tissue sample storage containers such as 12, 14, 16, 18, 20, 22, 24, 26, 28 and 30 disposed in a tray member 32. Unless otherwise indicated the tissue sample storage containers 12 through 30 are formed of a suitable flexible plastic material, preferably transparent, that is not deleteriously affected by preservative agents such as formaldehyde. Polystyrene, polyethylene or polypropylene have been found adequate for the purpose of this invention.

Figure 4:
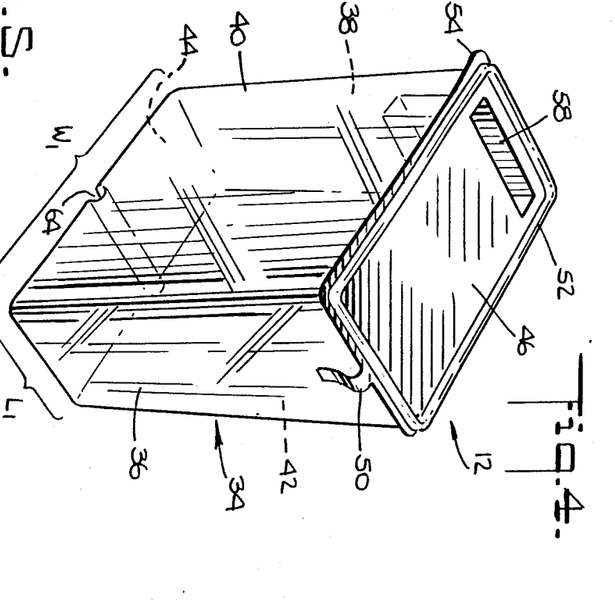
FIG. 4 is a perspective view of one embodiment of the tissue sample storage container.

Referring to FIG. 4, the tissue sample storage container has a hollow shell-like body 34 comprising wall portions 36, 38, 40 and 42. A base portion 44 is formed at one end of the shell 34 and a cover member 46 is provided at the opposite end thereof, such that an interior space 48 (FIG. 5) is defined within the container 12.

The cover member 46 is hinged to the wall portion 36 by a hinge 50 that can be molded integrally with the cover member 46. The hinge 50 can likewise be molded integrally with the shell portion 34 or suitably adhered to the wall portion 36. A detent channel 52 is formed at the periphery of the cover member 46 to grippingly engage the free ends of the wall portions 36, 38, 40 and 42 when the cover member 46 is in a closed position. A leak-tight seal is thus provided between the cover member 46 and the shell 34 when the cover member is in its closed position.

A tab or enlarged ear portion 54 (FIG. 4) is provided at a corner of the cover member 46 to facilitate displacement of the cover member 46 from the closed position of FIG. 4 to an open position (not shown) wherein the cover member 46 is disengaged from the free ends of the wall portions 36, 38, 40 and 42. With the cover member 46 in its open position, the free ends of the wall portions 36, 38, 40 and 42 define a mouth portion 56 of the container 12 through which the container can be filled or emptied.

The cover member 46 also includes a recess 58 that extends into the interior space 48 of the container 12 when the cover member 46 is in its closed position. The recess 58 accommodates a removable auxiliary container 60 having a detachable cover 62. The recess 58 does not have any openings that communicate with the interior space 48 enabling the auxiliary container 60 to be isolated from communication with the interior space 48.

The base portion 44 of the container 12 includes means for detachably gripping onto a rail and is formed with a elongated gripping recess 64 that extends across the side walls 40 and 42.

Figure 3:
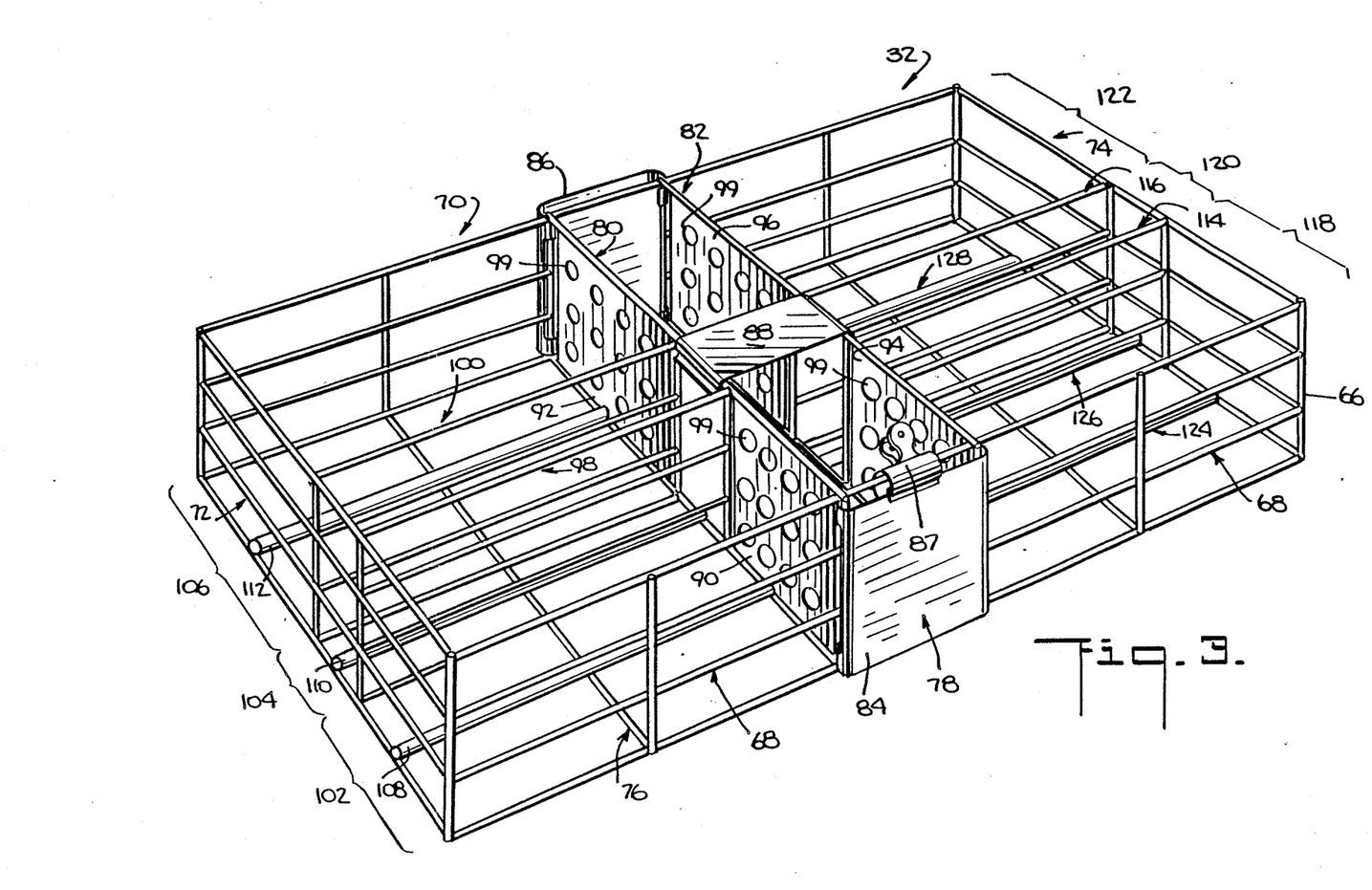
FIG. 3 is a perspective view of the tray member.

Referring to FIG. 3, the tray member 32 is in the form of a generally rectangular basket, preferably constructed of stainless steel wire as indicated at 66. Unless otherwise indicated, the structural components of the tray member 32 are formed of stainless steel. The tray member 32 has opposite side wall portions 68, 70 and 72, 74 joined by a base 76. A midsection 78 of the tray member 32 is defined by partitions 80 and 82 that extend from the side wall 68 to the side wall 70.

A pair of removable end plates 84 and 86, for the midsection 78, detachably clip onto the respective side walls 68 and 70 as most clearly shown in FIG. 3. A small spring clip 87 is provided at the end plate 84 for holding request forms or special attention notes pertaining to any of the specimens. A divider plate 88 for the midsection 78 detachably clips onto and bridges the partitions 80 and 82. Perforated sections 90 and 92 are secured in any suitable known manner to the partition 80, and corresponding perforated sections 94 and 96 ar similarly secured to the partition 82 such that the perforations 99 in the corresponding sections 90, 94 and 92, 96 are aligned.

A pair of wire partitions 98 and 100 extend from the side wall 72 to the partition 80, and define three container sections 102, 104 and 106. Each container section 102, 104 and 106 is provided with a respective rail 108, 110 and 112 at the base 76 of the tray member 32. The rail 108 is located approximately midway between the side wall 68 and the partition 98, whereas the rail 110 is located approximately midway between the partitions 98 and 100, and the rail 112 is located approximately midway between the partition 100 and the side wall 70.

A pair of wire partitions 114 and 116, similar to the partitions 98 and 100, extend from the side wall 74 to the partition 82 and define three additional container sections 118, 120 and 122. Each of the container sections 118, 120 and 122 are provided with a respective rail 124, 126 and 128 having midway locations similar to those described for the rails 108, 110 and 112. If desired each pair of rails 108, 124; 110, 126; and 112, 128 can be formed as a continuous rail. Also each pair of container sections 102, 118; 104, 120; and 106, 122 can be formed as respective continuous sections.

Figure 2:
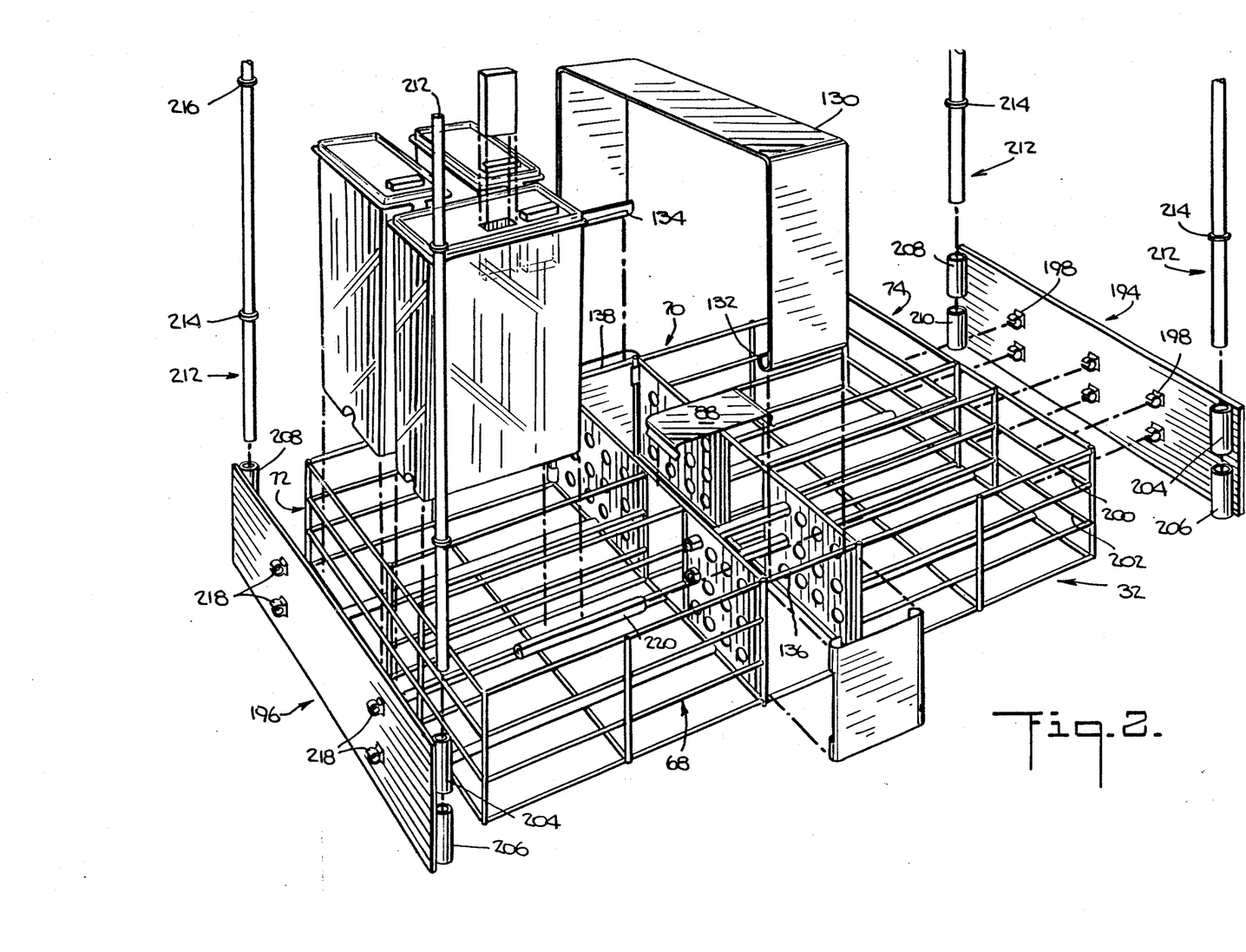
FIG. 2 is an exploded view thereof with some of the container members omitted for purposes of clarity.

Referring to FIG. 2, a U-shaped handle member 130 includes upturned free end portions 132 and 134 that detachably engage respective wire sections 136 and 138 of the side walls 68 and 70.

Figure 5:
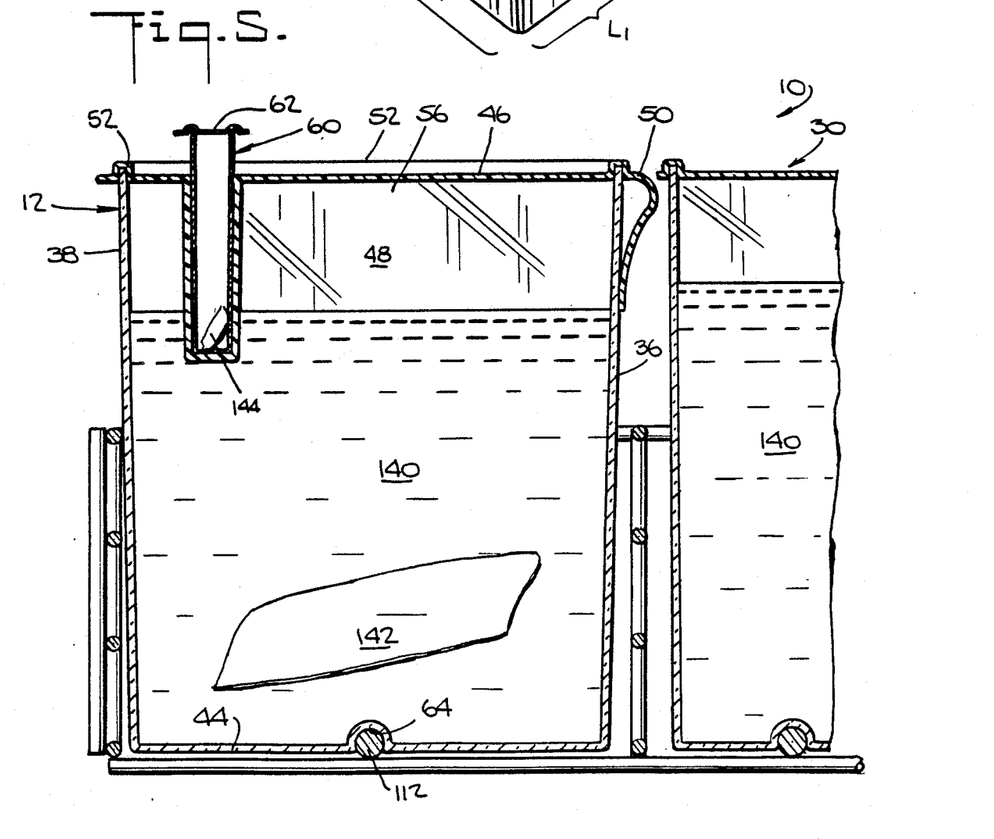
FIG. 5 is an enlarged fragmentary sectional view of the tissue sample storage system.

In using the tissue storage system 10, a preservative solution 140 such a formaldehyde is introduced into the interior space 48 of the container 12 through the mouth portion 56 when the cover member 46 is in an open position (not shown). The cover member 46 can be placed in an open position by grasping a peripheral portion thereof such as the ear portion 54 and lifting away from the shell 34. A tissue sample 142, such as shown in FIG. 5, can then be immersed in the preservative solution 140.

The container 12 is then closed by pressing the cover member detent channel 52 against the free end portions of the container walls 36, 38, 40 and 42. Under this arrangement the cover member 46 has a leak-tight securment to the shell 34 of the container 12.

The container 12 can then be disposed in the tray member 32 by aligning the gripper recess 64 of the base portion 44 with the rail 112 and forcing the container against the rail 112 such that the recess 58 grippingly accommodates the rail 112. If desired the recess 58 can be sized to permit slidable movement of the container 12 along the rail 112.

In numerous instances it is desirable to have more than one tissue sample 142 for separate individual testing. For example, a separate cutting 144 of the tissue sample 142 is located in the auxiliary container 60 that is disposed in the cover member 46 of the container 12.

Figure 7:
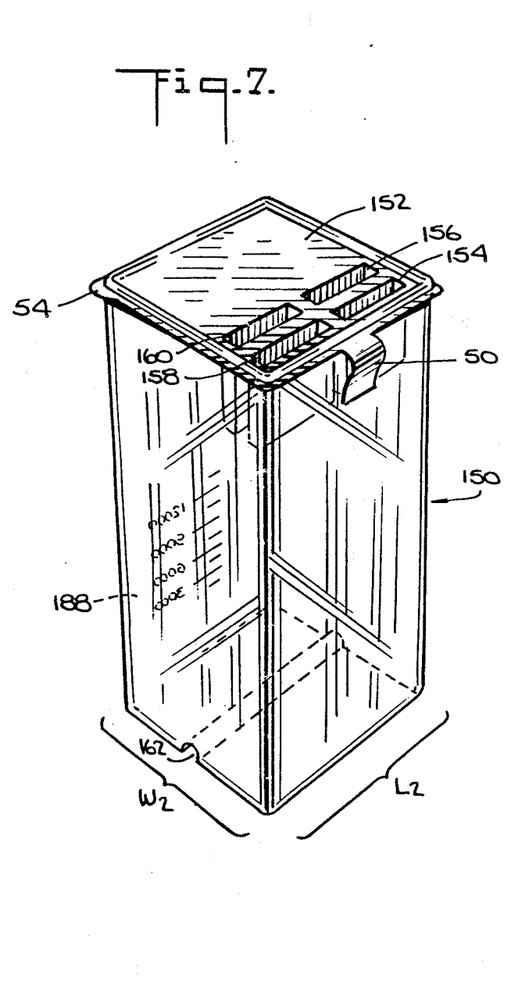
FIGS. 7 and 8 are other embodiments of the tissue sample storage container.

A container 150 as shown in FIG. 7 represents another embodiment of the invention. The container 150 has a cover member 152 having recesses 154, 156, 158 and 160 for accommodation of auxiliary containers (not shown) identical to the auxiliary container member 60. Although the recesses 154, 156, 158 and 160 are located toward the hinge 50 side of the container 150, it is often preferable to locate such recesses toward the ear portion 54 of the cover member 152. In all other respects except for differences in dimension, the container 150 operates in essentially the same fashion as the container 12. Thus the base recess 162 of the container 150 is of similar radius to the base recess 64 of the container 12 and both containers can be grippingly secured to any of the rails of the tray member 32.

To facilitate operation of the tissue storage system 10 it is preferred that the container sections 102, 104, 106, 118, 120 and 122 of the tray member 32 be of uniform width such as 6.3 centimeters and that the container members such as 12 (FIG. 4) and 150 (FIG. 7) likewise have uniform widths $W_1$ and $W_2$, such as for example 6 centimeters. However the lengths $L_1$ of the container 12 (FIG. 4) and $L_2$ of the container 150 (FIG. 7) can vary as a matter of choice. In addition, the heights of the respective containers 12 and 150 can be different as a matter of choice but should not exceed a predetermined maximum level. Under this arrangement tissue sample containers of any size can be disposed in any container section 102, 104, 106, 118, 120 and 122 of the tray member 32. For purposes of simplification the container heights can be limited to two sizes, such as 7 centimeters and 14 centimeters.

Figure 8:
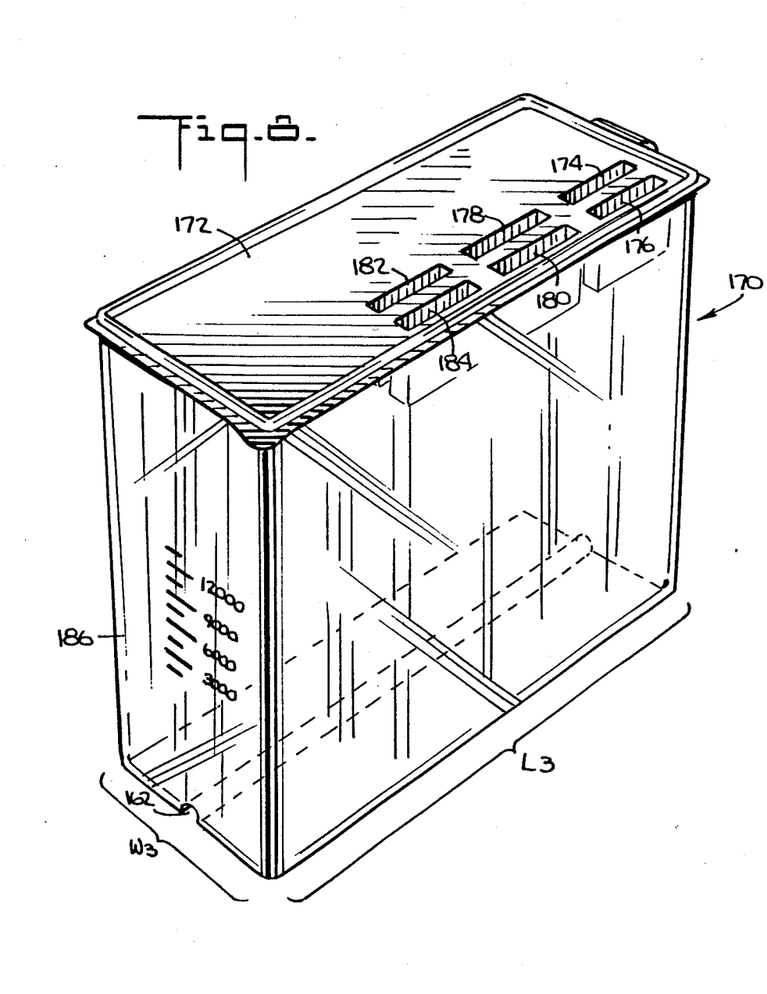

A container 170 representing another embodiment of this invention is shown in FIG. 8. The container 170 has a width $W_3$ equivalent to the width $W_2$ of the container 150 and a length $L_3$ greater than the length $L_2$ of the container 150. A cover member 172 of the container 170 includes six recesses 174, 176, 178, 180, 182 and 184 for accommodation of auxiliary containers 60 as shown in FIG. 5. The container member 170 also includes volumetric indicia 186 to indicate the volume of preservative held by the container 170. Corresponding volumetric indicia such as 188 (FIG. 7) can also be provided on the container 150 and on any other containers of the system 10. Operation and use of the container 170 is similar to that described for the containers 12 and 150.

Referring to FIG. 1, once the tray member 32 is filled to capacity with the tissue sample containers 12 through 30, it may be necessary to utilize a second tray member. Generally the tray members are used in areas where space is at a premium. Thus a further embodiment of the tissue storage system is generally indicated by the reference number 190 in FIG. 6.

Figure 6:
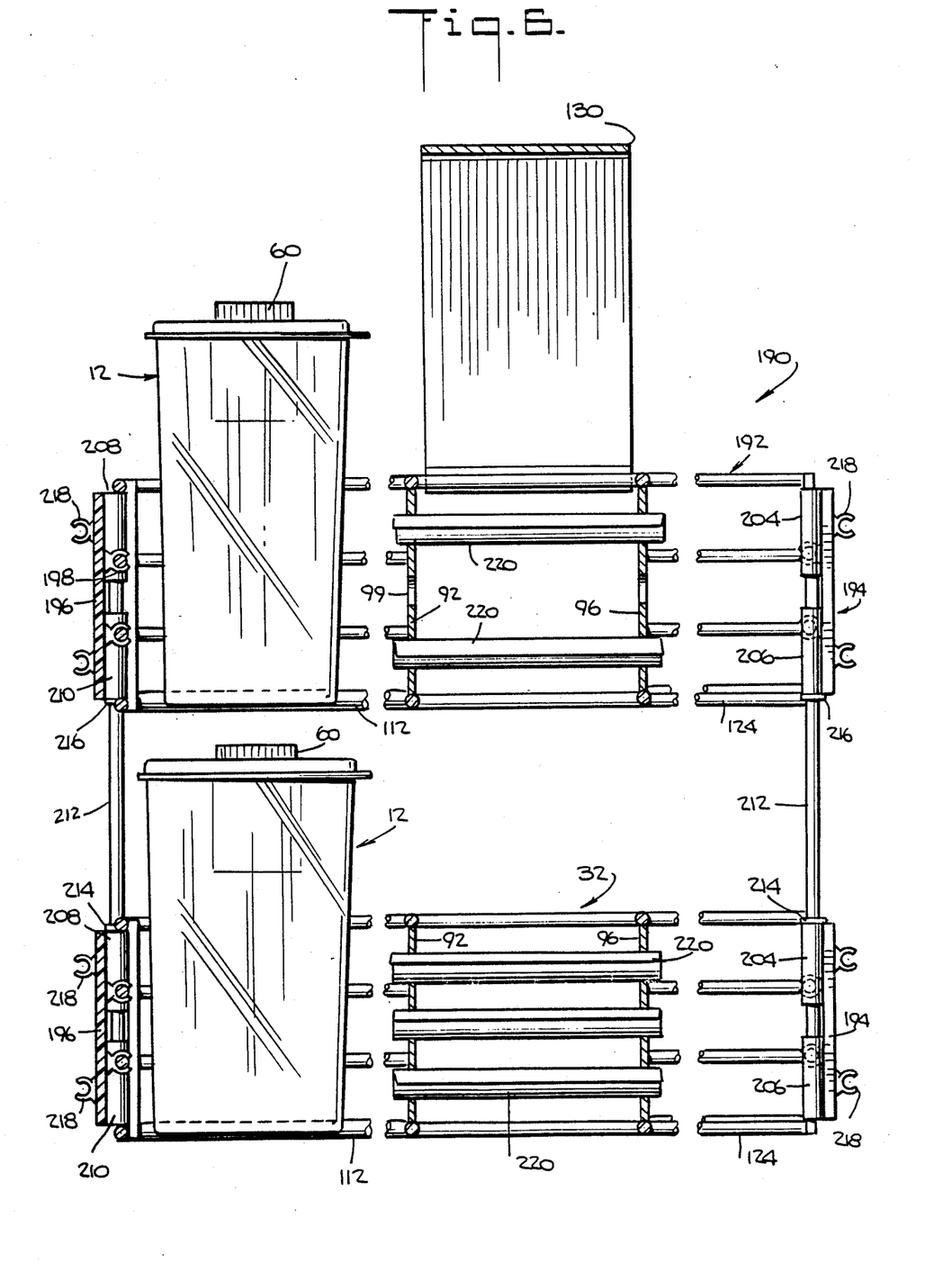
FIG. 6 shows the tissue sample storage system in stacked arrangement.

The tissue sample storage system 190 includes a tray member 192 stacked upon the tray member 32, the tray member 192 being identical to the tray member 32. Referring to FIG. 2, the tray member 32 is provided with a pair of oppositely disposed detachable side wall sections 194 and 196.

The side wall section 194 includes six jaw clips 198 formed of any suitable resilient plastic material and arranged to engage wire strips 200 and 202 of the side wall 74. The side wall section 194 also includes a pair of vertically aligned sleeves 204 and 206 at one end and another pair of vertically aligned sleeves 208 and 210 at an opposite end. The side wall section 194 is sized such that the vertically aligned sleeves 204, 206 and 208, 210 extend beyond the corners of the tray member 32 when the side wall section 194 is clipped onto the side wall 74 of the tray member 32. The sleeves 204, 206 and 208, 210 thus help to locate the side wall section 194 on the wall 74 of the tray member 32. Removal of the side wall section 194 from the tray member 32 is easily accomplished by grasping the sleeves 204, 206 and 208, 210 and pulling away from the tray member 32.

The side wall section 196 symmetrically corresponds to the side wall section 194 and also includes clips 198 and corresponding sleeves 204, 206 and 208, 210. The side wall section 196 is thus similarly secured to the wall 72 of the tray member 32.

Four corner spacer member rods 212 each include a pair of fixed spacer rings 214 and 216 spaced a predetermined amount from each other. The aligned sleeves 204, 206 and 208, 210 of each side wall section 194 and 196 accommodate a spacer member rod until the respective spacer rings 214 interfere with the respective sleeves 204 and 208 of the tray member 32 as shown in FIG. 6.

The tray member 192 has identical side wall sections 194 and 196 with aligned sleeves 204, 206 and 208, 210 that accommodate the upper end portions of the spacer member rods 212 until the sleeves 206 and 210 interfere with the spacer rings 216 as shown in FIG. 6. Thus the tray member 192 ca be stacked a predetermined distance from the tray member 32 corresponding to the spacing between the spacer rings 214 and 216. The maximum predetermined height of the tissue sample containers is selected so as to prevent interference between the containers and the tray members 32 and 192 when the tray members are stacked as shown in FIG. 6.

When there is no need for stacking of the tray members 32 and 192, the spacer member rods 212 can be stored in gripper jaw clips 218 provided on the outside of the side wall sections 194 and 196. It should be noted that the handle member 130 is omitted from the lower tray member 32 of the tissue storage system 190.

In either the tissue storage system 10 or the tissue storage system 190, the tissue sample containers include labels (not shown) affixed or adhesively secured to the top of each container after identifying data has been filled in. The perforated sections 90, 94 and 92, 96 accommodate documentation slips 220 that are rolled and stored in the perforations 99 of the tray members 32 and 192. The slips 220 can function as request or data slips, with one slip 220 being associated with each patient's tissue samples. The space below the divider plate 88 may be used to hold a packet of adsorbent material (not shown) to adsorb any preservative fumes that may be released.

Figure 9:
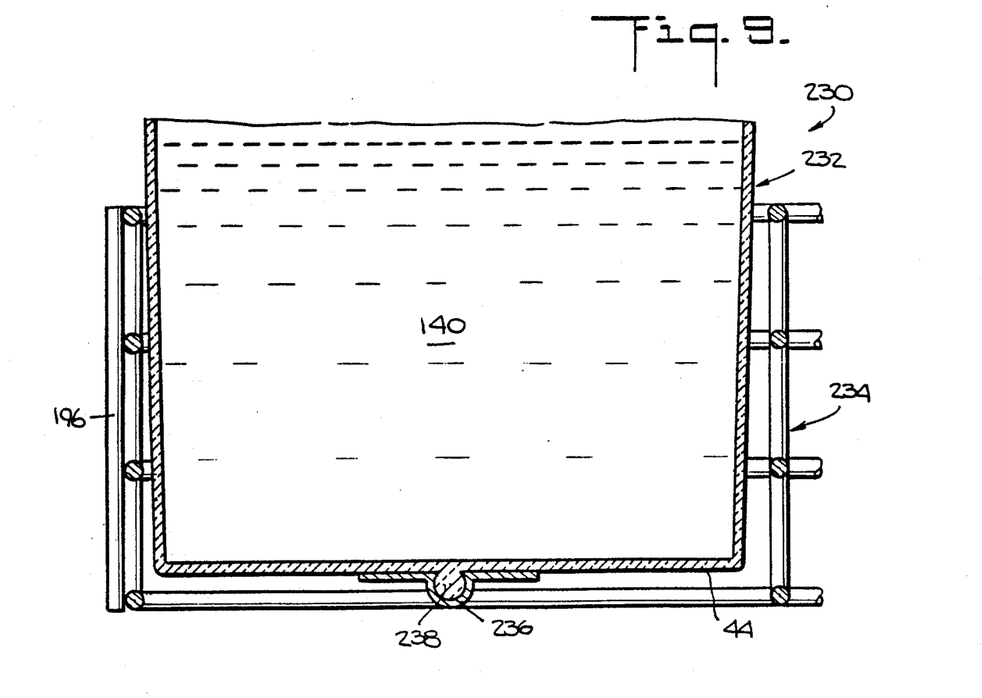
FIG. 9 is a fragmentary sectional view of another embodiment of the tissue sample storage system.

In another embodiment of the invention, a tissue storage system is generally indicated by the reference number 230 in FIG. 9. The tissue storage system 230 includes a tissue sample container 232 disposed in a tray member 234. The tray member 234 includes an elongated rail member 236 with a gripper recess that replaces rails 108, 110, 112, 124, 126 and 128 of the tray member 32. The tray member 234 is otherwise similar to the tray member 32.

The tissue sample container 232 includes a projection 238 at the base portion 44 and is otherwise similar in structure and operation to the tissue sample containers previously described for the tissue storage systems 10 and 190. Thus the tissue sample container 232 is detachably secured to the tray member 234 and the tray member 234 can be stacked to another similar tray member as previously described for the tray members 32 and 192.

Some advantages of the invention evident from the foregoing description include a tissue sample container that is detachably secured to a tray member, a tissue sample container that holds one or more auxiliary containers and a stacking capability for stacking one tray member onto another tray member.

In view of the above it will be seen that the several objects of the invention are achieved and other advantageous attained.

As various changes could be made in the above constructions without departing from the scope of the invention, it is intended that all matter contained in the above description or shown in the accompanying drawings shall be interpreted as illustrative and not in a limiting sense.

What is claimed is:

1. A tissue sample storage container comprising a hollow shell portion having opposite ends, a base at one end of said shell portion and a mouth portion at the opposite end of said shell portion, a cover member for closing said mouth portion when said cover member is in a closed position, such that said shell portion, said base and said cover member define an interior space of said container, said cover member being displaceable from said closed position to open said mouth portion, said cover member including at least one cover member recess defining a receiving space that is noncommunicable with the interior space of said container when said cover member is in said closed position, and wherein said cover member and said shell are formed of a plastic material, said container being of size to permit disposition in a portable tray with a plurality of other said containers and wherein said storage container includes at least one auxiliary container receivable in said recess, and said auxiliary container and said recess have complementary shaped cross sections.

2. The tissue sample storage container as claimed in claim 1, wherein said cover member recess extends into the interior space of said container when said cover member is in said closed position.

3. The tissue sample storage container as claimed in claim 1 wherein the plastic material is selected from the group consisting of polystyrene, polyethylene and polypropylene.

4. The tissue sample storage container as claimed in claim 3, wherein said cover member includes a plurality of said cover member recesses.

5. The tissue sample storage container as claimed in claim 4, wherein a corresponding plurality of said auxiliary containers are respectively receivable in said cover member recesses, said cover member recesses being sized to permit manual removal of said auxiliary containers from respective said cover member recesses.

6. The tissue sample storage container as claimed in claim 1 wherein the plastic material is transparent.

7. The tissue sample storage container as claimed in claim 1 wherein the plastic material is flexible.

8. The tissue sample storage container as claimed in claim 7 wherein said cover member and said shell include means for establishing a leak-tight seal at said mouth portion when said cover member is in said closed position.

9. The tissue sample storage container as claimed in claim 1, wherein said cover member is hinged to said shell portion.

10. A tissue sample storage container comprising a hollow shell portion having opposite ends, a base at one end of said shell portion and a mouth portion at the opposite end of said shell portion, a cover member for closing said mouth portion when said cover member is in a closed position, such that said shell portion, said base and said cover member define an interior space of said container, said cover member being displaceable from said closed position to open said mouth portion, said cover member including at least one cover member recess defining a receiving space that is noncommunicable with the interior space of said container when said cover member is in said closed position, and wherein said cover member and said shell are formed of a plastic material, said container being of size to permit disposition in a portable tray with a plurality of other said containers and wherein said storage container includes at least one auxiliary container receivable in said recess, said auxiliary container in said recess being sized to detent said auxiliary container in said recess and also permit manual removal of said auxiliary container from said recess when said auxiliary container is detented in said recess.

11. The tissue sample storage container as claimed in claim 10 wherein said cover member is hinged to said shell portion.

12. The tissue sample storage container as claimed in claim 10 wherein said cover member includes a plurality of said cover member recesses.

13. The tissue sample storage container as claimed in claim 12 wherein a corresponding plurality of said auxiliary containers are respectively receivable in said cover member recesses, said cover member recesses being sized to permit manual removal of said auxiliary containers from respective said cover member recesses.

14. The tissue sample storage container as claimed in claim 10 wherein said auxiliary container and said recess have complementary shaped cross sections.

15. A tissue sample storage container comprising a hollow shell portion having opposite ends, a base at one end of said shell portion and a mouth portion at the opposite end of said shell portion, a cover member for closing said mouth portion when said cover member is in a closed position, such that said shell portion, said base and said cover member define an interior space of said container, said cover member being displaceable from said closed position to open said mouth portion, said cover member including at least one cover member recess defining a receiving space that is noncommunicable with the interior space of said container when said cover member is in said closed position, and wherein said base portion includes means for detachable engagement with a rail.

16. The tissue sample storage container as claimed in claim 15, wherein said detachable engaging means comprise a base recess formed in said base portion.

17. The tissue sample storage container as claimed in claim 16, wherein said shell portion includes a pair of opposite side walls and said base recess extends into said opposite side walls.

18. The tissue sample storage container as claimed in claim 16, wherein said base recess, in cross section, defines a portion of a circle.

19. The tissue sample storage container as claimed in claim 15, wherein said detachable engaging means includes a base projection provided on said base portion.

20. A tissue sample storage container comprising a hollow shell portion having opposite ends, a base at one end of said shell portion and an opening at the opposite end of said shell portion, a cover member for covering said opening when said cover member is in a closed position, to define an interior space of said container for disposition of selected constituents, said cover member and said shell being formed of a plastic material, said cover member and said shell including flexible engaging means for forming a leak-tight seal around said opening to prevent said constituents in the interior space from passing out of the interior space when the cover member is in said closed position, said cover member being displaceable from said closed position to uncover said opening, and said cover member including a lid portion extending across said opening when said cover member is in said closed position, said cover member being formed with a hollow receptacle depending from said lid portion into the interior space of said container and being spaced from said shell, said receptacle being formed integrally with said lid portion to establish a leak-tight seal with said lid portion, and said receptacle having an interior receiving space that is noncommunicable with the interior space of said container when said cover member is in said closed position, said container including at least one auxiliary container receivable in said interior receiving space, said auxiliary container and said interior receiving space are sized to detent said auxiliary container in said interior receiving space and also permit manual removal of said auxiliary container from said interior receiving space when said auxiliary container is detented in said interior receiving space, said auxiliary container and said interior receiving space having complementary shaped cross sections.

21. A tissue sample storage container comprising a hollow shell portion having opposite ends, a base at one end of said shell portion and an opening at the opposite end of said shell portion, a cover member for closing said opening when said cover member is in a closed position such that said shell portion, said base portion and said cover member define an interior space of said container, said container including means for detachably gripping onto a rail, said detachable gripping means comprising a base recess formed in said base portion, said shell portion including a pair of opposite side walls and wherein said base recess extends into said opposite side walls.

* * * * *